United States Patent [19]

Lee et al.

[11] Patent Number: 4,841,074

[45] Date of Patent: Jun. 20, 1989

[54] INTERMEDIATES AND PROCESSES FOR 6-CARBOXY HMG-COA REDUCTASE INHIBITORS

[75] Inventors: Ta J. Lee; William F. Hoffman, both of Lansdale, Pa.

[73] Assignee: Merck & Co., Inc., Rahway, N.J.

[21] Appl. No.: 131,695

[22] Filed: Dec. 11, 1987

[51] Int. Cl.$^4$ ............................................. C07D 309/30
[52] U.S. Cl. .................................. 549/292; 549/281; 549/300; 514/460
[58] Field of Search ..................... 549/292, 281, 300; 514/460

[56] References Cited

U.S. PATENT DOCUMENTS

| | | | |
|---|---|---|---|
| 4,447,626 | 5/1984 | Terahara et al. | 549/292 |
| 4,582,915 | 4/1986 | Sleteinger et al. | 549/292 |
| 4,584,389 | 4/1986 | Sleteinger et al. | 549/292 |
| 4,604,472 | 8/1986 | Ide et al. | 549/292 |
| 4,719,229 | 1/1988 | Reamer et al. | 549/292 |
| 4,738,982 | 4/1988 | Arison et al. | 549/292 |
| 4,782,084 | 11/1988 | Vyas et al. | 549/292 |

OTHER PUBLICATIONS

Hesse, *Adv.* Free Radical Chem., 3, 83–137, (1969).
Barton, Pure Appl. Chem., 16 1–15 (1968).
Akhtar, Adv. Photochem., 2, 263–364 (1964).

*Primary Examiner*—Asok Pal
*Attorney, Agent, or Firm*—Melvin Winokur; Joseph F. DiPrima

[57] ABSTRACT

This invention discloses intermediates and a process for the preparation of 6-desmethyl-6-carboxy derivatives of lovastatin and analogs thereof at the 9-acyl side chain.

24 Claims, No Drawings

4,841,074

INTERMEDIATES AND PROCESSES FOR 6-CARBOXY HMG-COA REDUCTASE INHIBITORS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

Mevacor (lovastatin), now commercially available, is one of a group of very active antihypercholesterolemic agents that function by limiting cholesterol biosynthesis by inhibiting the enzyme, HMG-CoA reductase. In addition to the natural fermentation products, mevastatin and lovastatin, there are a variety of semi-synthetic and totally synthetic analogs thereof.

The naturally occurring compounds and their semi-synthetic analogs have the following general structural formulae:

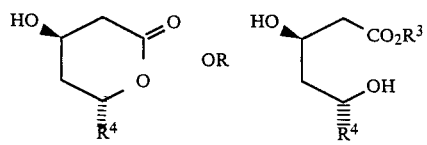

wherein:

$R^3$ is hydrogen, $C_{1-5}$ alkyl or $C_{1-5}$ alkyl substituted with a member of the group consisting of phenyl, dimethylamino, or acetylamino; and $R^4$ is

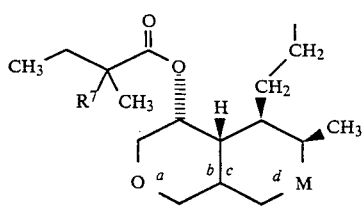

wherein Q is

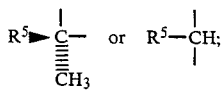

$R^5$ is H or OH; M is

$R^6$ is hydrogen or hydroxy;

$R^7$ is hydrogen or methyl; and a, b, c, and d represent single bonds, one of a, b, c or d represents a double bond, or both a and c or both b and d represent double bonds provided that when a is a double bond, Q is

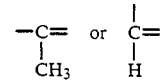

and when d is a double bond, M is

U.S. Pat. No. 4,517,373 discloses semi-synthetic hydroxy containing compounds represented by the above general formula wherein $R^4$ is

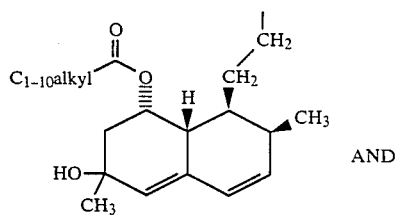

AND

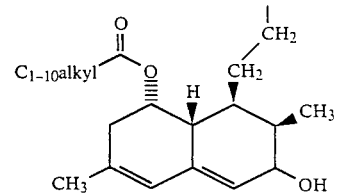

U.S. Pat. No. 4,537,859 and U.S. Pat. No. 4,448,979 also disclose semi-synthetic hydroxy-containing compounds represented by the above general formula wherein $R^4$ is

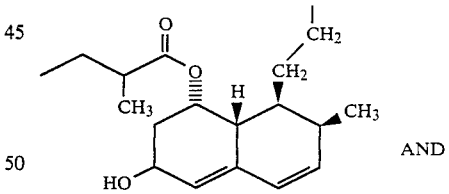

AND

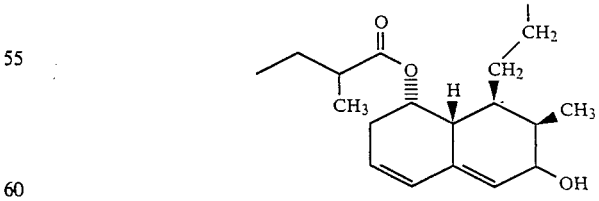

These compounds are prepared by the action of certain microorganisms on the corresponding non-hydroxylated substrates. One such organism described in U.S. Pat. No. 4,537,859 is of the genus Nocardia.

U.S. Pat. No. 4,376,863 discloses a fermentation product, isolated after cultivation of a microorganism belonging to the genus Aspergillus, which has a hydroxy containing butyryloxy side chain and is represented by the above general formula wherein $R^4$ is

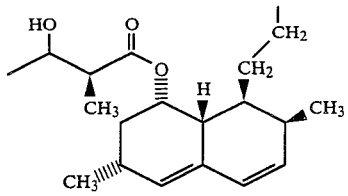

Japanese unexamined patent application J59-122,483-A discloses a semi-synthetic hydroxy-containing compound represented by the above general formula wherein $R^4$ is

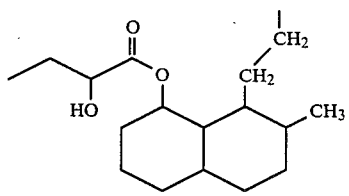

Copending U.S. patent application Ser. No. 048,136 filed May 15, 1987 discloses 6-substituted compounds of the above general formula wherein $R_4$ is

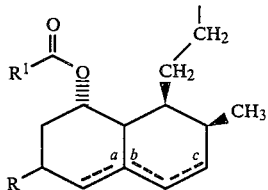

wherein R is $CH_2OH$,

, $CO_2R^4$ or

;

and $R^1$, $R^3$, $R^4$, $R^6$ and $R^7$ are broadly defined organic moieties.

The compounds of the above-mentioned U.S. patent application, Ser. No. 048,136 wherein a and c are double bonds were prepared by a microbiological conversion of lovastatin or an analog thereof with a 6-methyl substituent. Compounds where one of a, b or c represent a double bond or a, b, c all represent single bonds were prepared by a synthetic sequence from the 8-hydroxy-6-methyl derivative.

The literature discloses a reaction known as the Barton Reaction by which a hydrogen in the δ position to an OH group can be abstracted to afford a carbon radical which can be oxidized. (See Hesse Adv. Free-Radical Chem. 3, 83-137 (1969); Barton, Pure Appl. Chem. 16, 1-15 (1968); Arthar, Adv. Photochem. 2, 263-304 (1964).

DETAILED DESCRIPTION OF THE INVENTION

This invention relates to novel intermediates, and a novel process for their preparation, where said intermediates are useful in a novel preparation of 6-desmethyl-6-carboxy (I) derivatives of lovastatin and analogs thereof at the 8-acyl side chain. Said 6-carboxy derivatives of lovastatin and analogs thereof are useful in treating hypercholesterolemia and are disclosed in copending patent application, Ser. No. 048,136 filed May 15, 1987.

The overall process of this invention for preparing the 6-desmethyl-6-carboxy (I) derivatives of lovastatin is shown in scheme 1.

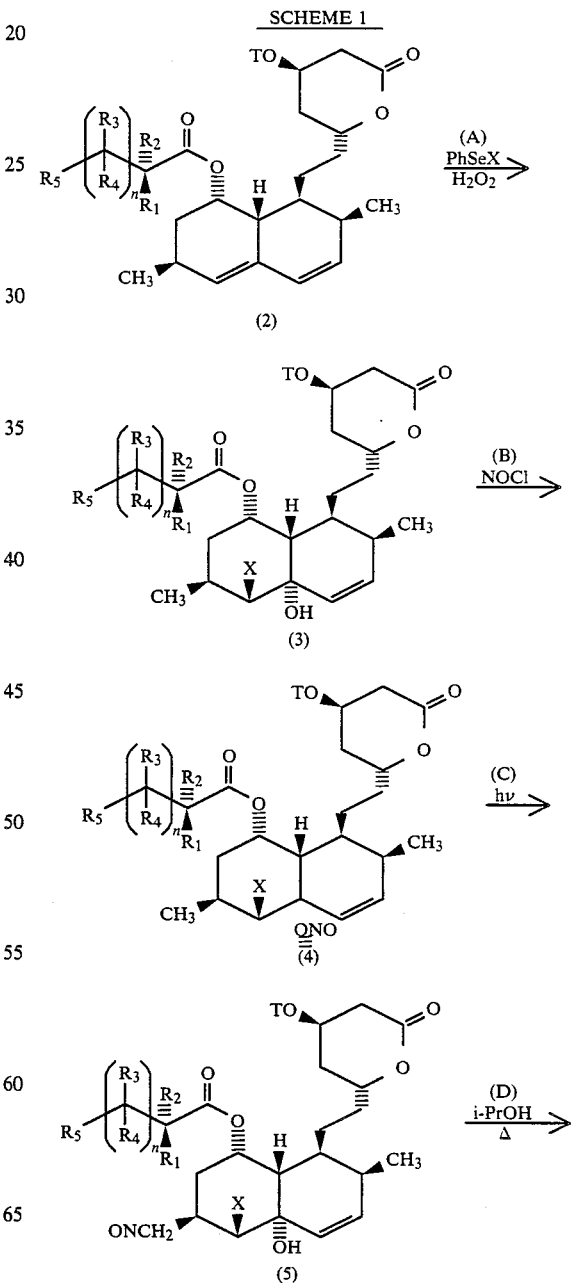

-continued
SCHEME 1

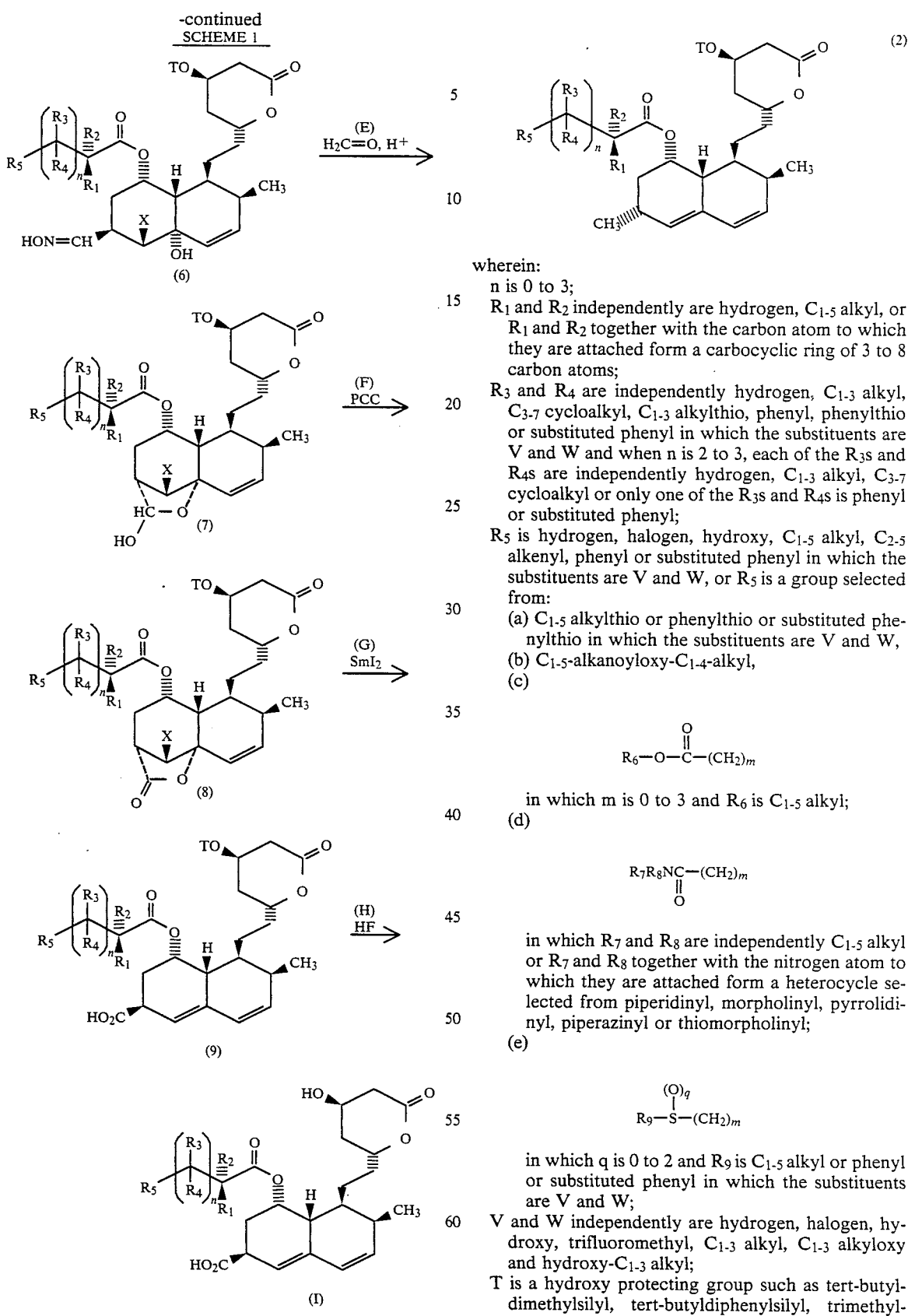

The intermediates (3) of the instant invention are prepared in a novel process (i) which comprises:

(A) contacting the compound (2)

wherein:

n is 0 to 3;

$R_1$ and $R_2$ independently are hydrogen, $C_{1-5}$ alkyl, or $R_1$ and $R_2$ together with the carbon atom to which they are attached form a carbocyclic ring of 3 to 8 carbon atoms;

$R_3$ and $R_4$ are independently hydrogen, $C_{1-3}$ alkyl, $C_{3-7}$ cycloalkyl, $C_{1-3}$ alkylthio, phenyl, phenylthio or substituted phenyl in which the substituents are V and W and when n is 2 to 3, each of the $R_3$s and $R_4$s are independently hydrogen, $C_{1-3}$ alkyl, $C_{3-7}$ cycloalkyl or only one of the $R_3$s and $R_4$s is phenyl or substituted phenyl;

$R_5$ is hydrogen, halogen, hydroxy, $C_{1-5}$ alkyl, $C_{2-5}$ alkenyl, phenyl or substituted phenyl in which the substituents are V and W, or $R_5$ is a group selected from:

(a) $C_{1-5}$ alkylthio or phenylthio or substituted phenylthio in which the substituents are V and W, (b) $C_{1-5}$-alkanoyloxy-$C_{1-4}$-alkyl, (c)

$$R_6-O-\overset{O}{\underset{\|}{C}}-(CH_2)_m$$

in which m is 0 to 3 and $R_6$ is $C_{1-5}$ alkyl;

(d)

$$R_7R_8N-\overset{O}{\underset{\|}{C}}-(CH_2)_m$$

in which $R_7$ and $R_8$ are independently $C_{1-5}$ alkyl or $R_7$ and $R_8$ together with the nitrogen atom to which they are attached form a heterocycle selected from piperidinyl, morpholinyl, pyrrolidinyl, piperazinyl or thiomorpholinyl;

(e)

$$R_9-\overset{(O)_q}{\underset{|}{S}}-(CH_2)_m$$

in which q is 0 to 2 and $R_9$ is $C_{1-5}$ alkyl or phenyl or substituted phenyl in which the substituents are V and W;

V and W independently are hydrogen, halogen, hydroxy, trifluoromethyl, $C_{1-3}$ alkyl, $C_{1-3}$ alkyloxy and hydroxy-$C_{1-3}$ alkyl;

T is a hydroxy protecting group such as tert-butyldimethylsilyl, tert-butyldiphenylsilyl, trimethylsilyl, triethylsilyl, triisopropylsilyl or tetrahydropyranyl;

with a halogenating agent such as a phenylselenyl halide or phenylsulfinyl chloride in an inert solvent at about $-80°$ C. then treating the product with an oxidizing agent such as hydrogen peroxide or a peroxyacid in an ethereal solvent at ambient temperature to yield a compound (3) wherein X=Cl or Br;

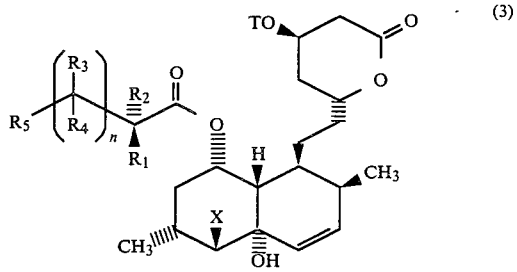
(3)

Intermediates (3) are used to form intermediates (7) in a process (ii) which comprises:

(B) reacting the compound (3) with nitrosyl chloride and a base to yield a compound (4);

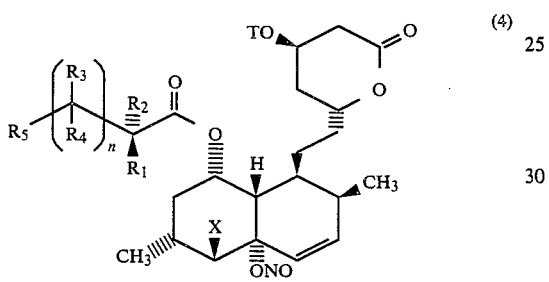
(4)

(C) irradiating the compound (4) with light to obtain compound (5);

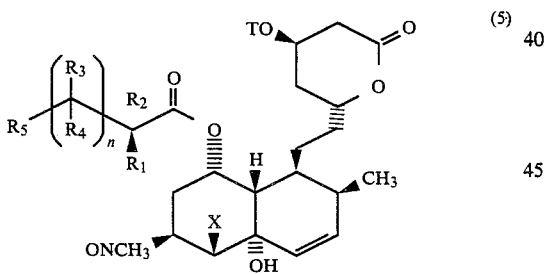
(5)

(D) heating the compound (5) in a protic solvent to afford compound (6);

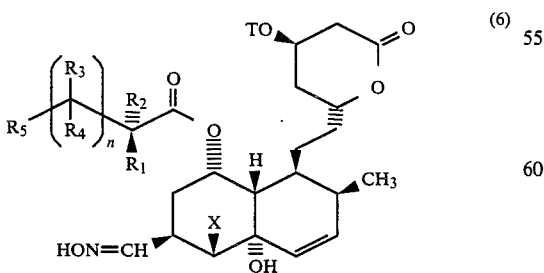
(6)

(E) treating compound (6) with an aqueous paraformaldehyde solution in the presence of an acid catalyst to yield a compound (7);

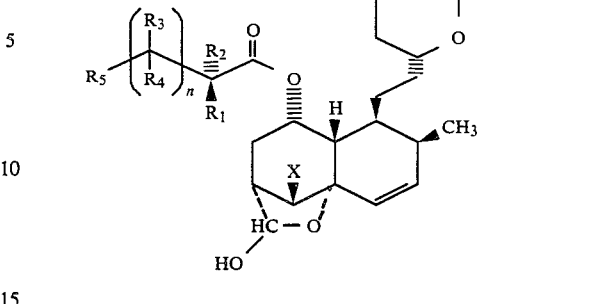
(7)

Intermediates (7) are used to form intermediates (8) in a novel process (iii) which comprises:

(F) contacting compound (7) with an oxidizing agent such as pyridinium chlorochromate (PCC) or chromium trioxide or chromium trioxide-pyridine or silver carbonate in an inert solvent to yield a compound (8);

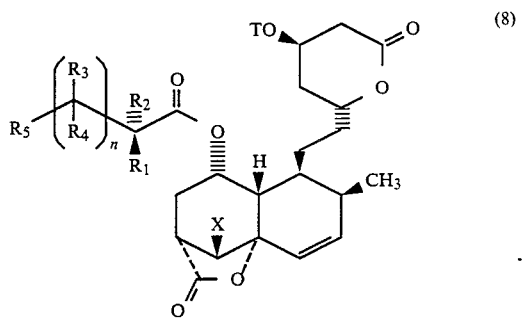
(8)

Intermediates (8) are used to form the 6-desmethyl-6-carboxy derivatives (I) of lovastatin and analogs thereof in a novel process (iv) which comprises:

(G) treating the compound (8) with samarium (II) iodide in an ethereal solvent to afford compound (9).

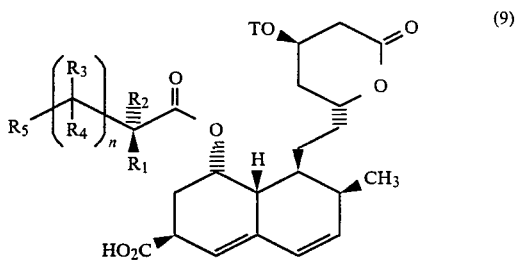
(9)

(H) Removal of the hydroxy-protecting group of compound (9) under standard acidic conditions such as an aqueous HF/CH$_3$CN mixture to afford product (I).

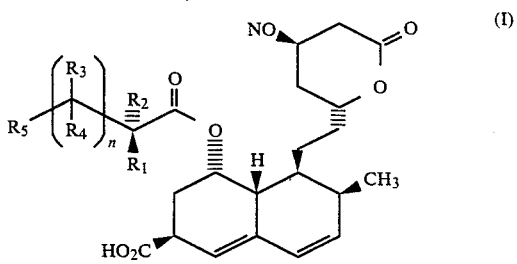
(I)

It should be understood that the alkyl, alkylthio, alkenyl and alkanoyl groups of this invention may either be in a straight chain or branched configuration.

One embodiment of this invention is the compounds of formula (3):

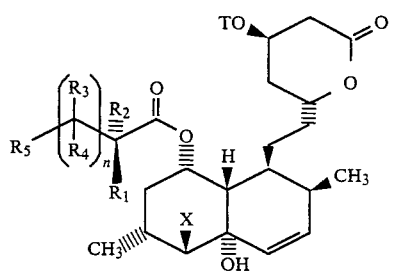

In one class of this embodiment are the compounds of formula (3) wherein:
$R_1$ is methyl;
$R_2$ is hydrogen or methyl;
$R_3$ and $R_4$ are independently hydrogen or $C_{1-3}$alkyl.
In a subclass:
$R_5$ is hydrogen, halogen, hydroxy, $C_{1-5}$alkyl, phenyl or substituted phenyl in which the substituents are V and W;
T is tert-butyldimethylsilyl; and X is Cl.
Exemplifying this subclass are compounds (3) wherein:
(1) n is 0, $R_2$ is methyl, $R_5$ is ethyl;
(2) n is 0, $R_2$ is hydrogen, $R_5$ is ethyl.

A second embodiment of this invention is the process for the preparation of intermediates (3) from the starting materials (2). This process consists of contacting a compound of formula (2) with a halogenating agent in an inert solvent followed by treatment with an oxidizing agent in an ethereal solvent.

A third embodiment of the instant invention is the compounds of formula (7):

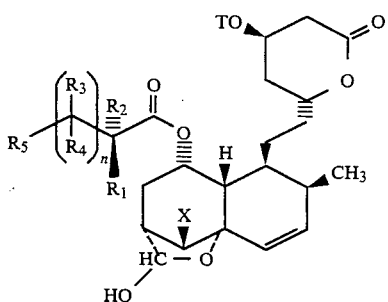

In one class of this embodiment are the compounds of formula (7) wherein:
$R_1$ is methyls
$R_2$ is hydrogen or methyl;
$R_3$ and $R_4$ are independently hydrogen or $C_{1-3}$ alkyl.
In a subclass:
$R_5$ is hydrogen, halogen, hydroxy, $C_{1-5}$alkyl, phenyl or substituted phenyl in which the substituents are V and W;
T is tert-butyldimethylsilyl; and X is Cl.
Exemplifying this subclass are compounds (7) wherein:
(1) n is 0, $R_2$ is methyl, $R_5$ is ethyl;
(2) n is 0, $R_2$ is hydrogen, $R_5$ is ethyl.

A fourth embodient of the instant invention is the compounds of formula (8):

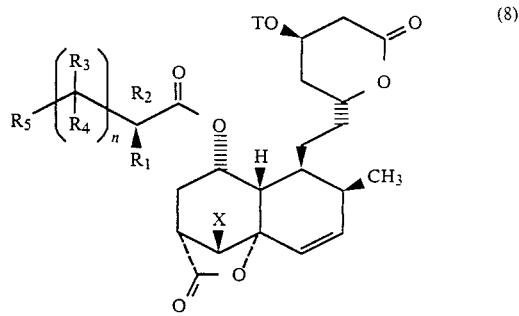

In one class of this embodiment are the compounds of formula (8) wherein:
$R_1$ is methyl;
$R_2$ is hydroen or methyl;
$R_3$ and $R_4$ are indpendently hydrogen or $C_{1-3}$alkyl.
In a subclass:
$R_5$ is hydrogen, halogen, hydroxy, $C_{1-5}$alkyl, phenyl or substituted phenyl in which the substituents are V and W;
T is tert-butyldimethylsilyl; and X is Cl.
Exemplifying this subclass are compounds (8) wherein:
(1) n is 0, $R_2$ is methyl, $R_5$ is ethyl;
(2) n is 0, $R_2$ is hydrogen, $R_5$ is ethyl.

A fifth embodiment of the instant invention is the process for the preparation of intermediates (8) from intermediates (7). This process consists in oxidizing a compound of formula (7) with an agent such as pyridinium chlorochromate or chromium trioxide or chromium trioxide-pyridine or silver carbonate.

A sixth embodiment of the present invention is the process for the preparation of intermediates (9) from intermediates (8). This process consists in contacting a compound of formula (8) with a samarium (II) halide, such as samarium (II) iodide in an ethereal solvent.

The diene (2) of step (A) is treated with a halogenating agent such as phenylselenyl chloride or bromide or phenylsulfinyl chloride, preferably phenylselenyl chloride, in an approximately equimolar ratio in an inert solvent at about −80° C., for approximately 20 minutes; illustrative of such inert solvents are methylene chloride, ether and the like. After a standard workup the product residue is dissolved in an ethereal solvent, chilled to about 0° C. and oxidized with an agent such as 30% hydrogen peroxide or a peroxy acid such as peroxybenzoic acid to yield a halohydrin analog (3). Compound (3) is treated with nitrosyl chloride at a temperature between −10° and 10° C., preferably 0° C. for several minutes in a basic solvent until TLC analysis of an aliquot showed the reaction to be complete. Illustrative of such basic solvents are pyridine and quinoline and the like.

The irradiation of a compound of formula (4) is conducted using light of wavelength greater than 320 Å. One source of the irradiation is a medium pressure mercury lamp, at a temperature between 0° and 30° C., preferably at about 20° C., for a period of from 0.5 to 5 hours, most preferably about 0.7 hours at 20° C., in an inert solvent such as benzene, pyridine, hexane or the like, or a mixture of inert solvents.

The rearrangement of a compound of formula (5) to a compound of formula (6) is conducted at a temperature between 60° and 100° C., preferably at 80° C. for a period of 0.5 to 10 hours, most preferably for 1 hour at about 80° C., in a protic solvent and an amine base. Illustrative of such protic solvents are alcohols such as isopropanol or 2-butanol and the like. Examples of amine bases are pyridine, triethylamine, quinoline, and the like.

The conversion of an oxime (6) to a lactol (7) is conducted using an approximately 40% aqueous paraformaldehyde solution and a carboxylic acid such as acetic acid.

The lactol (7) is oxidized with pyridinium chlorochromate ("PCC") or chromium trioxide or a chromium trioxide-pyridine complex or silver carbonate, preferably PCC in an inert solvent at about 25° C. for about 5 to 7 hours, preferably 7 hours. Illustrative of the inert solvents are methylene chloride, benzene and the like. The mole ratio of oxidizing agent to lactol (7) is approximately 2:1.

The samarium iodide is formed in situ by treating 1,2-diiodoethane with samarium powder in an ethereal solvent at about 25° C. for about 1 hour. The mole ratio of 1,2-diiodoethane to samarium powder is 1:2. The lactone (8) is treated with preformed samarium iodide at 25° to 80° C., preferably 75° C. for about 0.5 to 4 hours, preferably 1.5 hours, in an ethereal solvent. The mole ratio of lactone to samarium powder is approximately 1:2. Examples of such ethereal solvents are ethyl ether, tetrahydrofuran or dimethoxyethane.

The silyl ether or tetrahydropyranyl protecting group is removed by treating a compound (9) in acrtonitrile with an aqueous HF/CH$_3$CN mixture at about 0° C. for about 2.0 hours.

Starting material (2) wherein the acyl side chain is 2-methylbutyryloxy is obtained from lovastatin by reaction with a silyl chloride protecting group such as tert-butyldimethylsilyl chloride following the procedure in U.S. Pat. No. 4,444,784 or by treatment with dihydropyran to yield the tetrahydropyranyl protecting moiety. Lovastatin is prepared according to the fermentation procedure disclosed in U.S. Pat. No. 4,231,938.

Starting compounds (2) wherein the acyl side chain is other than 2-methylbutyryloxy are prepared from lovastatin by hydrolysis of the 8-acyl side chain, following the procedure in U.S. Pat. No. 4,444,784, followed by acylation with an appropriate alkanoyl chloride in the presence of lithium bromide and dimethylaminopyridine in pyridine using the procedure in copending U.S. Application Ser. No. 038,580 filed Apr. 15,1987. Alternatively, the acylation is conducted with an alkanoyl chloride or an alkanoic acid under standard reaction conditions.

The following examples illustrate the present invention and as such are not to be considered as limiting the invention set forth in the claims appended hereto.

EXAMPLE 1

Preparation of
6(R)-[2-[6(R)-carboxy-8(S)-(2,2-dimethylbutyryloxy)-2(S)-methyl-1,2,6,7,8,8a(R)-hexahydronaphthyl-1(S)]ethyl]-4(R)-hydroxy-3,4,5,6-tetrahydro-2H-pyran-2-one (I′)

(a)
6(R)-[2-[5(S)-Chloro-4a(S)-hydroxy-8(S)-(2,2-dimethylbutyryloxy)-2(S),6(R)-dimethyl-1,2,5,7,8,8a(S)-heptahydronaphthyl-1(S)]ethyl]-4(R)-(t-butyldimethylsilyloxy)-3,4,5,6-tetrahydro-2H-pyran-2-one (3′)

A solution of phenylselenyl chloride (10 g, 52 mmol) in methylene chloride (50 ml) was added dropwise to a stirred solution of 6(R)-[2-[8(S)-(2,2-dimethylbutyryloxy)-2(S),6(R)-dimethyl-1,2,6,7,-8,8a(R)-hexahydronaphthyl-1(S)]ethyl]-4(R)-(t-butyldimethylsilyloxy)-3,4,5,6-tetrahydro-2H-pyran-2-one (25.2 g, 48 mmol) in methylene chloride (350 ml) cooled in a dry ice/i-propanol bath (−78° C.). The resulting mixture was stirred at −78° C. for 20 mintues, poured into cold water (300 ml) and extracted with ether twice (400 ml, then 150 ml). The combined extracts were dried (MgSO$_4$), filtered and concentrated to afford an oily residue which was dissolved in tetrahydrofuran (300 ml). This solution was chilled in an ice bath (0° C.), and 30% hydrogen peroxide (15 ml) was added. The resulting mixture was stirred at 0° C. for 5 mintues, then warmed to room temperature and stirring continued for 1 hour. The reaction mixture was poured into cold water and extracted with chloroform three times (400 ml, then 2×100 ml). The combined extracts were dried (MgSO$_4$), filtered and concentrated to yield a residue which was purified by flash chromatography on a silica gel column. Elution with hexane:ethyl acetate (5:1/v:v) removed ay impurities. Further elution with hexane-ethyl acetate (4:1/v:v) provided the title compound as a pale yellow gum which later solidified on standing: mp 117°–8° C., nmr (CDCl$_3$) δ0.075 (3H, s), 0.08 (3H, s), 0.85 (3H, t, J=7 Hz), 0.88 (9H, s), 0.89 (3H, d, J=7 Hz), 1.15 (3H, s), 1.16 (3H, s), 1.32 (3H, d, J=7 Hz), 1.58 (2H, q, J=7 Hz), 3.39 (H, s), 4.05, (H, bs), 4.30 (H, m), 4.60 (H, m), 5.32 (H, m), 5.59 (H, d, J=11 Hz), 5.79 (H, d of d, J=11, 6 Hz). Anal. Calc'd for C$_{31}$H$_{53}$ClO$_6$Si: C, 63.61; H, 9.13 Found: C, 63.80; H, 9.04

(b)
6(R)-[2-[5(S)-Chloro-4a(S)-nitrosyloxy-8(S)-(2,2-dimethylbutyryloxy)-2(S),6(R)-dimethyl-1,2,5,6,7,8,8a(S)-heptahydronaphthyl-1(S)]ethyl]-4(R)-(t-butyldimethylsilyloxy)-3,4,5,6-tetrahydro-2H-pyran-2-one (4′)

Nitrosyl chloride gas was passed through a solution of compound 3′ (4 g, 6.83 mmol) in pyridine (40 ml) at 0° C. for several mintues and the reaction became a dark brown colored mixture. An aliquot was taken and partitioned between ether and water. When TLC analysis[1] of the ether layer indicated the reaction to be complete, the reaction mixture was poured into an ice/water mixture (ca. 100 ml) and extracted with benzene (150 ml). The organic phase was separated and the aqueous phase was extracted with another portion of benzene (50 ml). The combined extracts were then dried (MgSO$_4$) and filtered. The filtrate[2] was diluted with benzene to a volume of ca. 530 ml and used immediately in the subsequent photolysis.

[1]When eluted with hexane:ethyl acetate (v:v/4:1), the R$_f$ values of the starting compound 3′ and product 4′ are 0.25 and 0.39, respectively.

[2] The amount of pyridine present in this solution was not determined. The presence of pyridine is critical for the stabilization of compound 4'.

(c)
6(R)-[2-[5(S)-Chloro-4a(S)-hydroxy-8(S)-(2,2-dimethylbutyryloxy)-2(S)-methyl-6(S)-nitrosylmethyl-1,2,5,6,7,8,8a(S)-heptahydronaphthyl-1(S)]ethyl]-4(R)-(t-butyldimethylsilyloxy)-3,4,5,6-tetrahydro-2H-pyran-2-one (5')

A solution of compound 4' in benzene and pyridine, freshly prepared from compound 3' (4 g, 6.83 mmol) as described in step (b) was deoxygenated by bubbling nitrogen gas through the solution for 10 minutes. Then, it was irradiated (450 W Hanovia medium pressure mercury lamp, pyrex sleeve) at room temperature for 40 minutes while nitrogen continued to bubble through the solution. The photolyzed solution was transferred to a 500 ml R-B flask and concentrated in vacuo to a volume of ca. 25 ml. This residue was diluted with ether and shaken with dilute hydrochloric acid (1N, 150 ml) to remove pyridine. After washing with water (100 ml) and 5% sodium bicarbonate solution, the solution was dried (MgSO$_4$) and filtered. Evaporation of the filtrate left a residue which was purified by flash chromatography. Elution with hexane:ethyl acetate (v:v/4:1) removed side products. Then, elution with hexane-ethyl acetate (v:v/2:1) gave 6(R)-[2-[5(S)-chloro-4a(S)-hydroxy-8(S)-(2,2-dimethylbutyryloxy)-2(S)-methyl-6(S)-hydroxyiminomethyl-1,2,5,6,7,8,8a(S)-heptahydronaphthyl-1(S)]ethyl]-4(R)(t-butyldimethylsilyloxy)-3,4,5,6-tetrahydro-2H-pyran-2-one (6'), and compound 5' as an off-white solid: m.p. 155°-7° C. (decomp.); nmr (CDCl$_3$) δ0.07 (3H, s), 0.08 (3H, s), 0.86 (3H, t, J=7 Hz), 0.9 (9H, s), 0.95 (3H, d, J=7 Hz), 1.18 (3H, s), 1.20 (3H, s), 2.84 (H, s), 2.91 (H, m), 4.18 (H, s), 4.30 (H, m), 4.36 (H, d of d, J=10, 7 Hz), 4.60 (H, m), 4.94 (H, d of d, J=10, 7 Hz), 5.27 (H, m), 5.56 (H, d, J=10 Hz), 6.81 (H, d of d, J=10, 6 Hz).
Anal. Calc'd for C$_{31}$H$_{52}$ClNO$_7$Si: C, 60.61; H, 8.53; N, 2.28
Found: C, 60.77; H, 8.75; N, 2.59

(d)
6(R)-[2-[5(S)-Chloro-4a(S)-hydroxy-8(S)-(2,2-dimethylbutyryloxy)-2(S)-methyl-6(S)-hydroxyiminomethyl-1,2,5,6,7,8,8a(S)-heptahydronaphthyl-1(S)]ethyl]-b 4(R)-(t-butyldimethylsilyloxy)-3,4,5,6-tetrahydro-2H-pyran-2-one (6')

Pyridine (1.5 ml) was added to a stirred solution of compound 5' (5.66 g, 9.21 mmol) in i-propanol (150 ml). The resulting mixture was heated at reflux for 1 hour. After cooling, the reaction mixture was concentrated in vacuo to afford the title compound as a foamy gum: nmr (CDCl$_3$) δ0.08 (3H, s), 0.90 (9H, s), 3.12 and 3.64 (H, both m), 4.30 (H, m), 4.30 and 4.38 (H, both s), 4.60 (H, m), 5.28 and 5.23 (H, both m), 5.57 (H, d, J=10 Hz), 5.84 (H, d, J=10, 6 Hz), 7.21 and 7.75 (H, both d, J=6 Hz), 7.32 (H, bs).

(e)
6(R)-[2-[5(S)-Chloro-6(S)-formyl-4a(S)-hydroxy-2(S)-methyl-8(S)-(2,2-dimethylbutyryloxy)-1,2,5,6,7,8,8a(S)-heptahydronaphthyl-1(S)]ethyl]-4(R)-(t-butyldimethylsilyloxy)-3,4,5,6-tetrahydro-2H-pyran-2-one, lactol (7')

A 40% aqueous paraformaldehyde solution[3] (250 ml) and acetic acid (0.53 ml, 9.28 mmol) were added to a solution of the oxime 6' (5.7 g, 9.28 mmol) in acetone (350 ml) and the cloudy reaction mixture was stirred at ambient temperature overnight. The acetone was removed in vacuo at 30° C. and the aqueous residue was extracted with ether (3×100 ml). The ether extracts were combined, washed with saturated NaHCO$_3$ solution (25 ml), H$_2$O (25 ml), brine (2×25 ml) and dried over MgSO$_4$. Filtration and evaporation in vacuo gave the crude lactol 7' as a tan foam which was used in Step f without further purification: nmr (CDCl$_3$) δ0.87 (9H, s), 1.15 (3H, s), 1.17 (3H, s), 2.58 (2H, m), 4.28 (H, m), 4.49 (H, d, J=4 Hz), 4.56 (H, m), 5.14 (H, m), 5.39 (H, d, J=10 Hz), 5.42 (H, s), 6.14 (H, d of d, J=10, 6 Hz).
[3] 40% aqueous paraformaldehyde solution was prepared by refluxing a mixture of paraformaldehyde (100 g) in H$_2$O (250 ml) for 1.5 hours (oil bath=130° C.). The reaction was cooled and filtered to remove some gelatinous polymer.

(f)
6(R)-[2-[6(S)-Carboxy-5(S)-chloro-4a(S)-hydroxy-2(S)-methyl-8(S)-(2,2-dimethylbutyryloxy)-1,2,5,6,7,8,8a(S)-heptahydronaphthyl-1(S)]ethyl]-4(R)-(t-butyldimethylsilyloxy)-3,4,5,6-tetrahydro-2H-pyran-2-one, lactone (8')

A solution of the lactol 7' (2.05 g, 3.42 mmol) in CH$_2$Cl$_2$ (20 ml) was added to a stirred suspension of pyridinium chlorochromate (1.47 g, 6.84 mmol) in CH$_2$Cl$_2$ (100 ml) and the mixture was stirred at ambient temperature. After 7 hours[4], the reaction was diluted with ether and the resulting mixture was filtered. The solid residue was stirred in ether (2×100 ml) and filtered. The filtrates were combined and concentrated in vacuo to a semisolid (2.1 g) which was purified by flash chromatography on a 4×15 cm column of silica gel (230-400 mesh). The column was eluted with acetone/CH$_2$Cl$_2$ (1:99/v:v) to give the lactone 8' as a colorless solid, m.p. 166°-8° C: nmr (CDCl$_3$) δ0.063 (3H, s), 0.074 (3H, s), 0.82 (3H, t, J=7 Hz), 0.87 (9H, s), 0.92 (3H, d, J=7 Hz), 1.12 (3H, s), 1.14 (3H, s), 2.79 (H, m), 4.29 (H, m), 4.35 (H, d, J=5 Hz), 4.55 (H, m), 5.26 (H, m), 5.42 (H, d, J=10 Hz), 6.27 (H, d of d, J=10, 6 Hz).
Anal. Calc'd for C$_{31}$H$_{49}$ClO$_7$Si: C, 62.33; H, 8.27
Found: C, 62.49; H, 8.40
[4] The reaction was followd by TLC [Whatman Silica gel 60 A, EtOAc-hexane (3:7)] R$_f$ of 7'=0.2, R$_f$ of 8'=0.4.

(g)
6(R)-[2-[6(R)-Carboxy-8(S)-(2,2-dimethylbutyryloxy)-2(S)-methyl-1,2,6,7,8,8a(R)-hexahydronaphthyl-1(S)]ethyl]-4(R)-(t-butyldimethylsilyloxy)-3,4,5,6-tetrahydro-2H-pyran-2-one, (9')

A THF[5] solution (25 ml) of 1,2-diiodoethane[6] (2.55 g, 9.04 mmol) was added dropwise to magnetically-stirred samarium powder (2.72 g, 18.08 mmol), contained in an oven-dried flask, at a rate sufficient to maintain a gentle reflux under a nitrogen atmosphere. After stirring an additional 45 minutes at ambient temperature, a THF solution (25 ml) of the lactone 8' (2.7 g, 4.52 mmol) was added and the reaction was heated in a 75° C. oil bath for 1.5 hours[7]. The reaction was cooled to 0° C. (ice-/acetone bath) and slowly treated with 5% HCl (max. temp.=10° C.) until acidic (pH=4). The resulting mixture was stirred 10 minutes at 0° C. and poured into ether (100 ml). The aqueous layer was extracted with 2×100 ml ether and the ether extracts were combined, washed with brine (25 ml) and dried over MgSO$_4$. Filtration and evaporation gave the acid 9' as a pale yellow foam. A portion of the acid was purified by flash chromatography on silica gel (230-400 mesh) column. Elution with isopropanol/hexane (1:9/v:v) provided the acid as a colorless solid, m.p. 111°-113° C: nmr (CDCl$_3$) δ0.070 (3H, s), 0.078 (3H, s), 0.79 (3H, t, J=7 Hz), 0.88

(9H, s), 1.03 (3H, s), 1.05 (3H, s), 3.21 (H, m), 4.28 (H, m), 4.58 (H, m), 5.33 (H, m), 5.74 (H, m), 5.87 (H, d of d, J=10, 6 Hz), 6.05 (H, d, J=10 Hz).

Anal. Calc'd for $C_{30}H_{50}O_7Si$: C, 66.15; H, 8.96
Found: C, 66.02; H, 8.97

[5] THF was distilled under nitrogen from sodium benzophenone ketyl.
[6] An ether solution of 1,2-diiodoethane was washed with aqueous sodium thiosulfate solution and water and then dried over $MgSO_4$. Filtration and evaporation gave a colorless solid which was stored in the freezer.
[7] The reaction was followed by TLC [Whatman Silica gel 60 A, EtOAc-hexane (3:7)]. $R_f$ of 8'=0.4, $R_f$ of 9'=0.0 to 0.17.

(h)

6(R)-[2-[6(R)-carboxy-8(S)-(2,2-dimethylbutyryloxy)-2(S)-methyl-1,2,6,7,8,8a(R)-hexahydronaphthyl-1(S)]ethyl]-4(R)-hydroxy-3,4,5,6-tetra-hydro-2H-pyran-2-one (I')

A solution of 48% $HF/CH_3CN$ (1:19/V:V, 1 ml) was added to a magnetically stirred $CH_3CN$ solution (2 ml) of the silyl ether 9' (8 mg, 0.015 mmol). The solution was stirred under ambient conditions for 2.0 hours and then poured into ether (50 ml). The ether solution was washed with saturated $NaHCO_3$ solution (5 ml), brine (2×10 ml) and dried over $MgSO_4$. Filtration and evaporation gave the desilylated lactone I' as a viscous oil which was purified by flash chromatography on a 1×7 cm column of silica gel (230–400 mesh). Elution of the column with isopropanol-hexane (1:4/V:V) removed the less polar impurities. Further elution with isopropanol-HOAc (19:1/V:V) provided the title compound: nmr ($CDCl_3$) δ 0.80 (3H, t, J=7 Hz), 1.04 (3H, s), 1.07 (3H, s), 3.24 (H, m), 4.38 (H, m), 4.60 (H, m), 5.38 (H, m), 5.78 (H, m), 5.87 (H, dd, J=10, 6 Hz), 6.05 (H, d, J=10 Hz), 8.55 (H, bm).

What is claimed is:

1. A compound of structural formula (3):

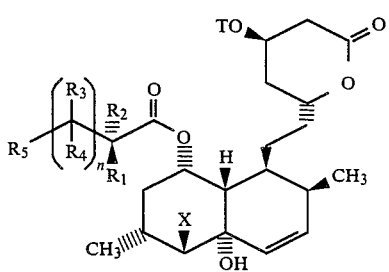

(3)

wherein
n is 0 to 3;
$R_1$ and $R_2$ independently are hydrogen, $C_{1-5}$alkyl, or $R_1$ and $R_2$ together with the carbon atom to which they are attached form a carbocyclic ring of 3 to 8 carbon atoms;
$R_3$ and $R_4$ are independently hydrogen, $C_{1-3}$ alkyl, $C_{3-7}$ cycloalkyl, $C_{1-3}$ alkylthio, phenyl, phenylthio or substituted phenyl in which the substituents are V and W and when n is 2 to 3, each of the $R_3$s and $R_4$s are independently hydrogen, $C_{1-3}$ alkyl, $C_{3-7}$ cycloalkyl or only one of the $R_3$s and $R_4$s is phenyl or substituted phenyl;
$R_5$ is hydrogen, halogen, hydroxy, $C_{1-5}$ alkyl, $C_{2-5}$ alkenyl, phenyl or substituted phenyl in which the substituents are V and W, or $R_5$ is a group selected from:
(a) $C_{1-5}$ alkylthio or phenylthio or substituted phenylthio in which the substituents are V and W,
(b) $C_{1-5}$-alkanoyloxy-$C_{1-4}$-alkyl, (c)

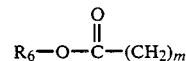

in which m is 0 to 3 and $R_6$ is $C_{1-5}$ alkyl;

(d)

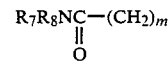

in which $R_7$ and $R_8$ are independently $C_{1-5}$ alkyl or $R_7$ and $R_8$ together with the nitrogen atom to which they are attached form a heterocycle selected from piperidinyl, morpholinyl, pyrrolidinyl, piperazinyl or thiomorpholinyl;

(e)

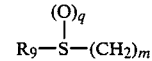

in which q is 0 to 2 and $R_9$ is $C_{1-5}$alkyl or phenyl or substituted phenyl in which the substituents are V and W;
V and W independently are hydrogen, halogen, hydroxy, trifluoromethyl, $C_{1-3}$alkyl, $C_{1-3}$ alkyloxy and hydroxy-$C_{1-3}$alkyl;
T is tert-butyldimethylsilyl, tert-butyldiphenylsilyl, trimethylsilyl, triethylsilyl, triisopropylsilyl or tetrahydropyranyl;
X is Cl or Br.

2. A compound of claim 1 wherein:
$R_1$ is methyl;
$R_2$ is hydrogen or methyl;
$R_3$ and $R_4$ are independently hydrogen or $C_{1-3}$alkyl.

3. A compound of claim 2 wherein:
$R_5$ is hydrogen, halogen, hydroxy, $C_{1-5}$ alkyl, phenyl or substituted phenyl in which the substituents are V and W;
T is tert-butyldimethylsilyl; and X is Cl.

4. A compound of claim 3 selected from the group wherein:
(a) n is 0, $R_2$ is methyl, $R_5$ is ethyl;
(b) n is 0, $R_2$ is hydrogen, $R_5$ is ethyl.

5. A compound of structural formula (7):

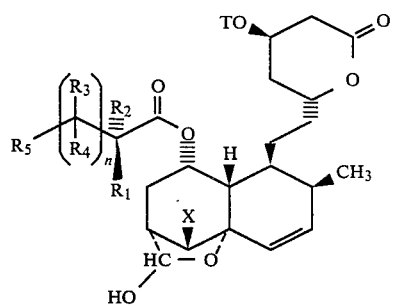

(7)

wherein:
n is 0 to 3;
$R_1$ and $R_2$ independently are hydrogen, $C_{1-5}$ alkyl, or $R_1$ and $R_2$ together with the carbon atom to which they are attached form a carbocyclic ring of 3 to 8 carbon atoms;

R$_3$ and R$_4$ are independently hydrogen, C$_{1-3}$ alkyl, C$_{3-7}$ cycloalkyl, C$_{1-3}$ alkylthio, phenyl, phenylthio or substituted phenyl in which the substituents are V and W and when n is 2 to 3, each of the R$_3$s and R$_4$s are independently hydrogen, C$_{1-3}$ alkyl, C$_{3-7}$ cycloalkyl or only one of the R$_3$s and R$_4$s is phenyl or substituted phenyl;

R$_5$ is hydrogen, halogen, hydroxy, C$_{1-5}$ alkyl, C$_{2-5}$ alkenyl, phenyl or substituted phenyl in which the substituents are V and W, or R$_5$ is a group selected from:
(a) C$_{1-5}$ alkylthio or phenylthio or substituted phenylthio in which the substituents are V and W,
(b) C$_{1-5}$-alkanoyloxy-C$_{1-4}$-alkyl,
(c)

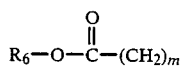

in which m is 0 to 3 and R$_6$ is C$_{1-5}$ alkyl;
(d)

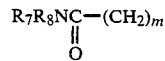

in which R$_7$ and R$_8$ are independently C$_{1-5}$ alkyl or R$_7$ and R$_8$ together with the nitrogen atom to which they are attached form a heterocycle selected from piperidinyl, morpholinyl, pyrrolidinyl, piperazinyl or thiomorpholinyl;
(e)

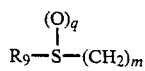

in which q is 0 to 2 and R$_9$ is C$_{1-5}$ alkyl or phenyl or substituted phenyl in which the substituents are V and W;

V and W independently are hydrogen, halogen, hydroxy, trifluoromethyl, C$_{1-3}$ alkyl, C$_{1-3}$ alkyloxy and hydroxy-C$_{1-3}$ alkyl;

T is tert-butyldimethylsilyl, tert-butyldiphenylsilyl, trimethylsilyl, triethylsilyl, triisopropylsilyl or tetrahydropyranyl;

X is Cl or Br.

6. A compound of claim 5 wherein:
R$_1$ is methyl;
R$_2$ is hydrogen or methyl;
R$_3$ and R$_4$ are independently hydrogen or C$_{1-3}$ alkyl.

7. A compound of claim 6 wherein:
R$_5$ is hydrogen, halogen, hydroxy, C$_{1-5}$ alkyl, phenyl or substituted phenyl in which the substituents are V and W;
T is tert-butyldimethylsilyl; and X is Cl.

8. A compound of claim 7 selected from the group wherein:
(a) n is 0, R$_2$ is methyl, R$_5$ is ethyl;
(b) n is 0, R$_2$ is hydrogen, R$_5$ is ethyl.

9. A compound of structural formula (8):

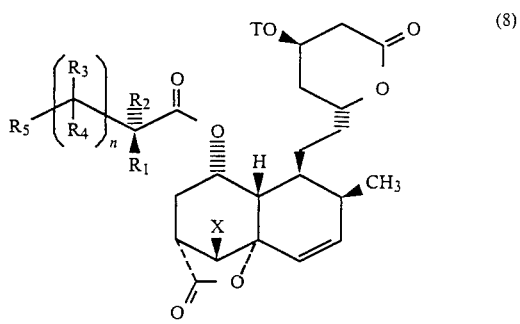

(8)

wherein:
n is 0 to 3;
R$_1$ and R$_2$ independently are hydrogen, C$_{1-5}$ alkyl, or R$_1$ and R$_2$ together with the carbon atom to which they are attached form a carbocyclic ring of 3 to 8 carbon atoms;
R$_3$ and R$_4$ are independently hydrogen, C$_{1-3}$ alkyl, C$_{3-7}$ cycloalkyl, C$_{1-3}$ alkylthio, phenyl, phenylthio or substituted phenyl in which the substituents are V and W and when n is 2 to 3, each of the R$_3$s and R$_4$s are independently hydrogen, C$_{1-3}$ alkyl, C$_{3-7}$ cycloalkyl or only one of the R$_3$s and R$_4$s is phenyl or substituted phenyl;

R$_5$ is hydrogen, halogen, hydroxy, C$_{1-5}$ alkyl, C$_{2-5}$ alkenyl, phenyl or substituted phenyl in which the substituents are V and W, or R$_5$ is a group selected from:
(a) C$_{1-5}$ alkylthio or phenylthio or substituted phenylthio in which the substituents are V and W,
(b) C$_{1-5}$-alkanoyloxy-C$_{1-4}$-alkyl,
(c)

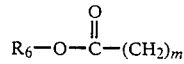

in which m is 0 to 3 and R$_6$ is C$_{1-5}$ alkyl;
(d)

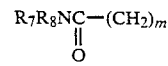

in which R$_7$ and R$_8$ are independently C$_{1-5}$ alkyl or R$_7$ and R$_8$ together with the nitrogen atom to which they are attached form a heterocycle selected from piperidinyl, morpholinyl, pyrrolidinyl, piperazinyl or thiomorpholinyl;
(e)

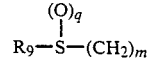

in which q is 0 to 2 and R$_9$ is C$_{1-5}$ alkyl or phenyl or substituted phenyl in which the substituents are V and W;

V and W independently are hydrogen, halogen, hydroxy, trifluoromethyl, C$_{1-3}$ alkyl, C$_{1-3}$ alkyloxy and hydroxy-C$_{1-3}$ alkyl;

T is tert-butyldimethylsilyl, tert-butyldiphenylsilyl, trimethylsilyl, triethylsilyl, triisopropylsilyl or tetrahydropyranyl;

X is Cl or Br.

10. A compound of claim 9 wherein:

$R_1$ is methyl;

$R_2$ is hydrogen or methyl;

$R_3$ and $R_4$ are independently hydrogen or $C_{1-3}$ alkyl.

11. A compound of claim 10 wherein:

$R_5$ is hydrogen, halogen, hydroxy, $C_{1-5}$ alkyl, phenyl or substituted phenyl in which the substituents are V and W;

T is tert-butyldimethylsilyl; and X is Cl.

12. A compound of claim 11 selected from the group wherein:

(a) n is 0, $R_2$ is methyl, $R_5$ is ethyl;

(b) n is 0, $R_2$ is hydrogen, $R_5$ is ethyl.

13. A process for the preparation of a compound of claim 1 which comprises:

(a) contacting a compound of formula (2)

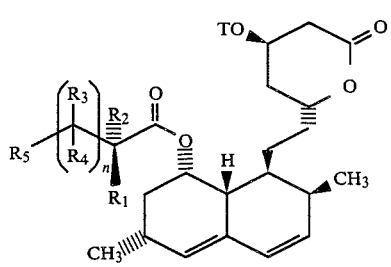

(2)

with a halogenating agent in an inert solvent and then treating the product with an oxidizing agent in an ethereal solvent, to yield a compound of formula (3).

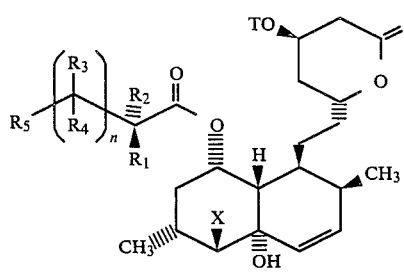

(3)

14. A process of claim 13 wherein the halogenating agent is selected from phenylselenyl chloride, phenylselenyl bromide or phenylsulfinyl chloride and the oxidizing agent is selected from 30% hydrogen peroxide, peroxybenzoic acid or peracetic acid.

15. A process of claim 14 wherein the halogenating agent is phenylselenyl chloride, the oxidizing agent is 30% hydrogen peroxide, and X is Cl.

16. A process for the preparation of a compound of claim 9 which comprises: contacting a compound of formula (7)

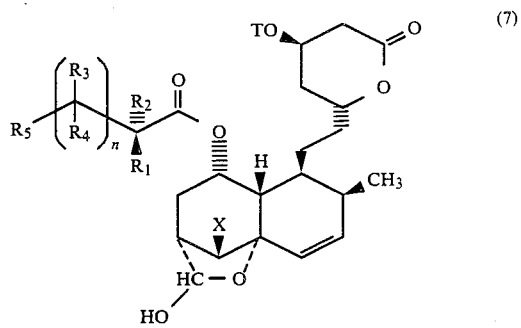

(7)

with an oxidizing agent in an inert solvent to yield a compound of formula (8)

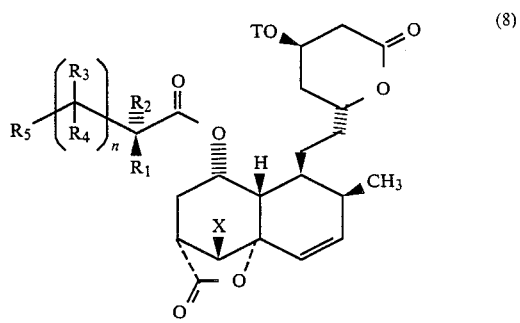

(8)

17. A process of claim 16 wherein the oxidizing agent is selected from: pyridinium chlorochromate ("PCC") or chromium trioxide or chromium trioxide-pyridine or silver carbonate.

18. A process of claim 17 wherein the oxidizing agent is pyridinium chlorochromate.

19. A process for the preparation of a compound (9)

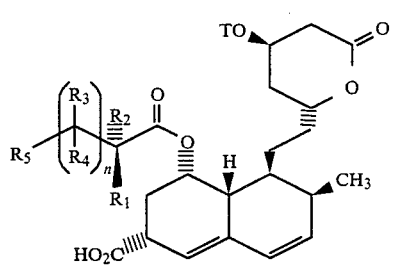

(9)

which commprises: treating a compound (8)

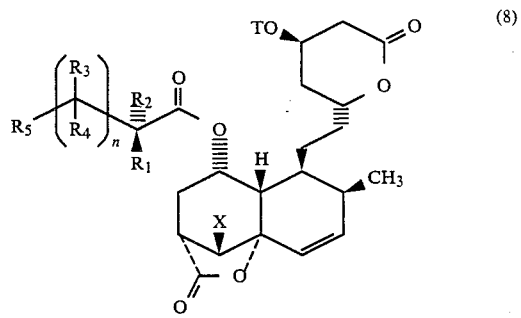

(8)

with samarium (II) iodide in an ethereal solvent at about 25° C.

20. A process of claim 19 wherein the ethereal solvent is selected from ethyl ether or tetrahydrofuran or dimethoxyethane.

21. A process of claim 19 which further comprises:
(a) contacting a compound (2);

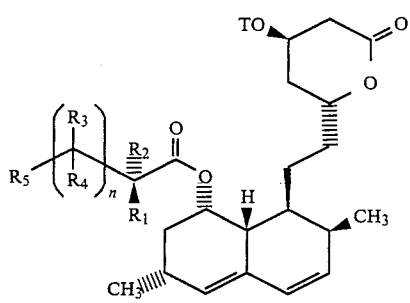
(2)

with phenylselenyl chloride or phenylselenyl bromide (X=Cl or Br) at about −80° C. in methylene chloride followed by treatment with 30% hydrogen peroxide in tetrahydrofuran at about 25° C. to yield a compound (3); then

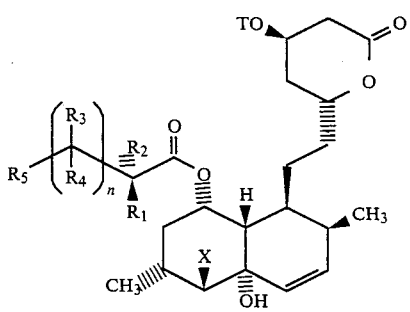
(3)

(b) reacting the compound (3) with nitrosyl chloride in pyridine to yield a compound (4);

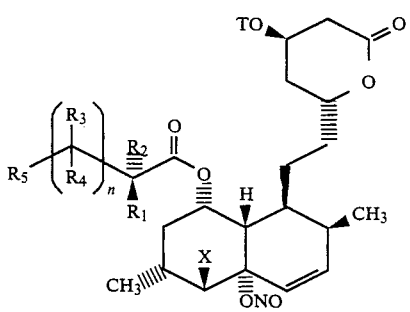
(4)

(c) irradiating the compound (4) with light of wavelength greater than 320 Å in benzene-pyridine to yield a compound (5);

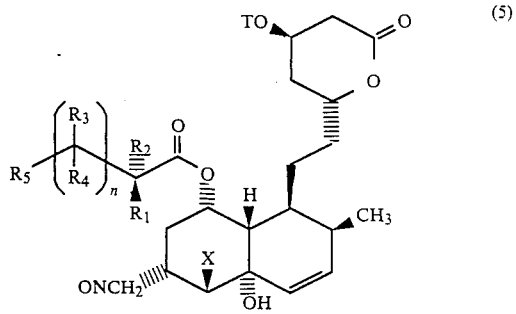
(5)

(d) heating the compound (5) in isopropanol at about 80° C. to afford compound (6); then

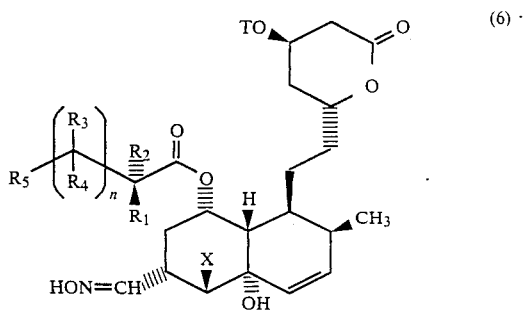
(6)

(e) treating compound (6) with an aqueous paraformaldehyde solution in the presence of an acid catalyst to yield a compound (7);

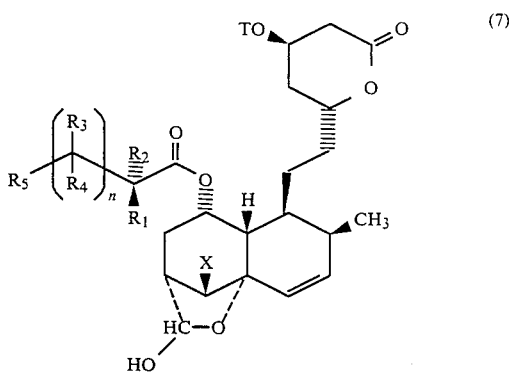
(7)

(f) contacting a compound (7) with pyridinium chlorochromate in methylene chloride to yield a compound (8).

22. A process of claim 21 wherein:
$R_1$ is methyl;
$R_2$ is hydrogen or methyl;
$R_3$ and $R_4$ are independently hydrogen or $C_{1-3}$ alkyl.

23. A process of claim 22 wherein:
$R_5$ is hydrogen, halogen, hydroxy, $C_{1-5}$ alkyl, phenyl or substituted phenyl in which the substituents are V and W;
T is tert-butyldimethylsilyl; and X is Cl.

24. A process of claim 23 wherein the compound (9) is selected from the group wherein:
(a) n is 0, $R_2$ is methyl, $R_5$ is ethyl;
(b) n is 0, $R_2$ is hydrogen, $R_5$ is ethyl.

* * * * *